United States Patent [19]

Nakada et al.

[11] Patent Number: 4,867,141
[45] Date of Patent: Sep. 19, 1989

[54] MEDICAL TREATMENT APPARATUS UTILIZING ULTRASONIC WAVE

[75] Inventors: Akio Nakada; Syuichi Takayama; Tatsuya Kubota; Tetsumaru Kubota; Koji Taguchi; Shinichi Imade; Naomi Sekino, all of Tokyo, Japan

[73] Assignee: Olympus Optical Co., Ltd., Tokyo, Japan

[21] Appl. No.: 61,862

[22] Filed: Jun. 12, 1987

[30] Foreign Application Priority Data

| Jun. 18, 1986 [JP] | Japan | 61-141864 |
| Jun. 20, 1986 [JP] | Japan | 61-144510 |
| Jun. 20, 1986 [JP] | Japan | 61-144513 |
| Jun. 20, 1986 [JP] | Japan | 61-144516 |
| Nov. 28, 1986 [JP] | Japan | 61-283563 |

[51] Int. Cl.$^4$ .............................. A61H 1/00
[52] U.S. Cl. .................. 128/24 A; 604/22; 128/328
[58] Field of Search .............. 604/22; 128/328, 24 A, 128/303.14, 303.15, 305

[56] References Cited

U.S. PATENT DOCUMENTS

| 3,805,787 | 4/1974 | Banko | 128/276 |
| 3,830,240 | 8/1974 | Antonevich et al. | |
| 3,927,675 | 12/1975 | Pohlman et al. | |
| 4,169,984 | 10/1979 | Parisi | 128/24 A |
| 4,227,532 | 10/1980 | Bluhm et al. | 128/328 |
| 4,425,115 | 1/1984 | Wuchinich | 604/22 |
| 4,741,731 | 5/1988 | Starck et al. | 128/24 A |

Primary Examiner—Max Hindenburg
Assistant Examiner—Scott M. Getzow
Attorney, Agent, or Firm—Frishauf, Holtz, Goodman & Woodward

[57] ABSTRACT

A medical treatment apparatus utilizing ultrasonic waves according to this invention is applied to treatments such as breaking up a stone formed in a living body. The medical treatment apparatus utilizing ultrasonic waves includes a vibration generator (10) for generating ultrasonic vibrations and a vibration transmission member (16) for transmitting the ultrasonic vibrations generated by the vibration generator (10). The vibration transmission member (16) has a front end portion and a proximal end portion which is mounted on the vibration generator (10). The medical treatment apparatus further includes a cover member (20) for surrounding the outer surface of the vibration transmission member (16) and an exposing member (21) for exposing the distal end portion of the vibration transmission member (16) outside the cover member (20). When the vibration transmission member (16) is inserted into an endoscope channel and a body cavity, the distal end of vibration transmission member (16) does not damage them since the distal end is sealed with the cover (20).

8 Claims, 13 Drawing Sheets

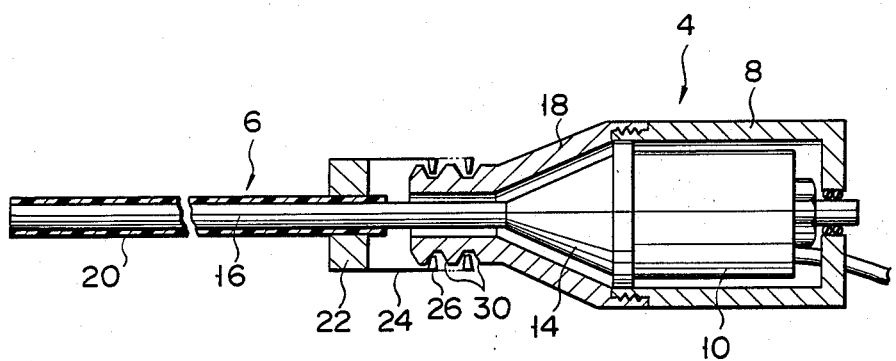
F I G. 4
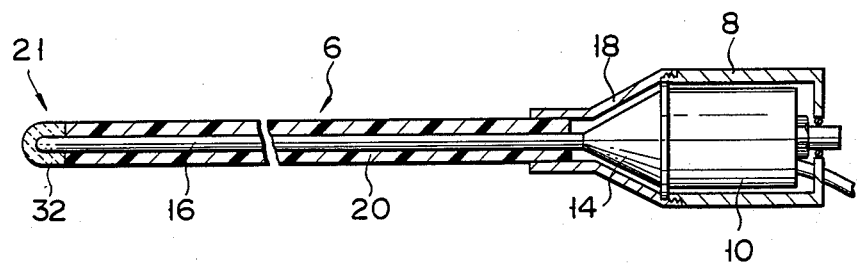
F I G. 5
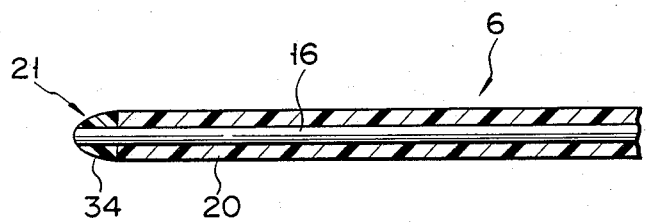
F I G. 6

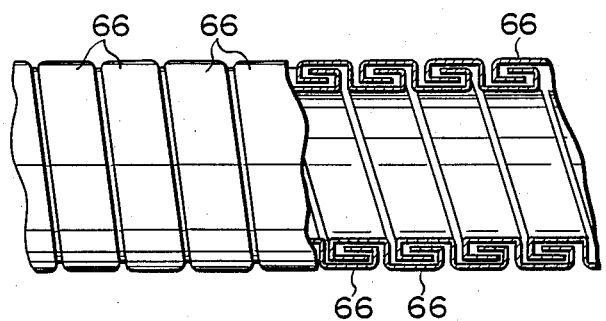
F I G. 12
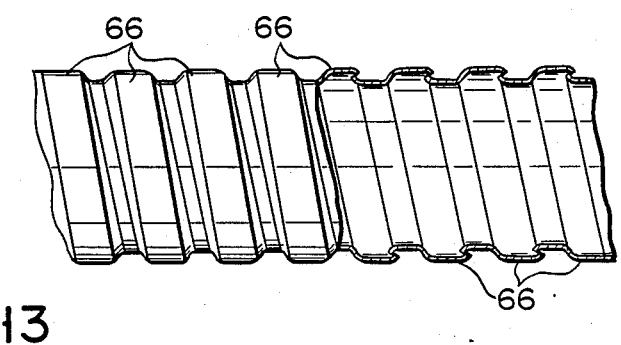
F I G. 13
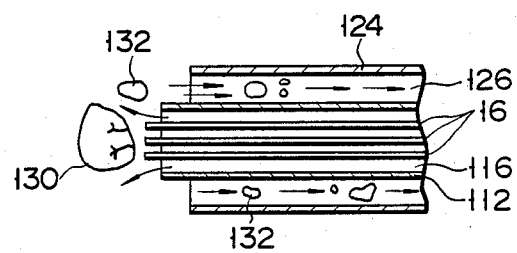
F I G. 15
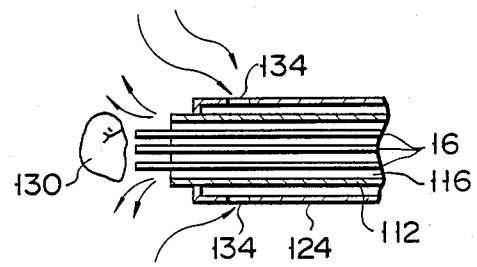
F I G. 16

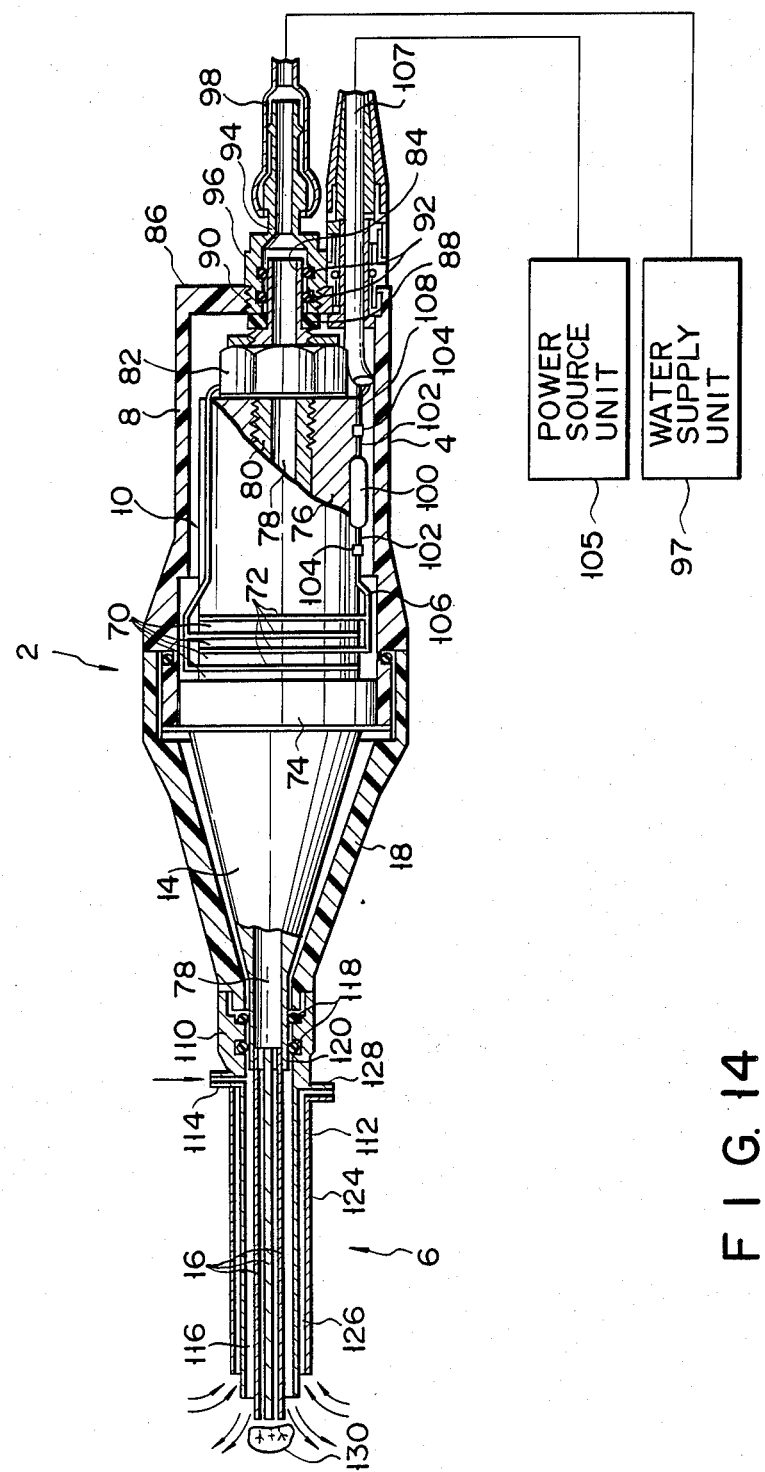
F I G. 14

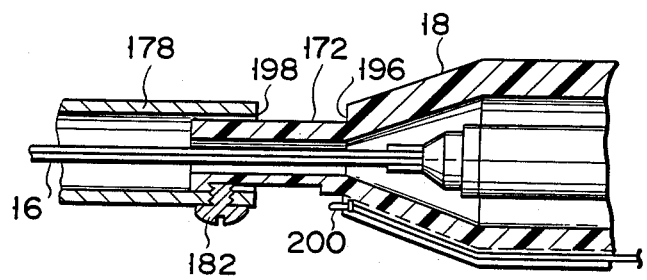
F I G. 25
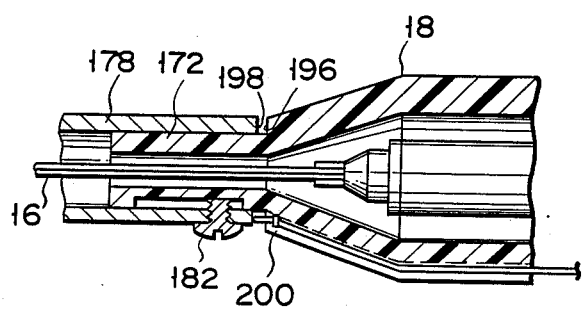
F I G. 26
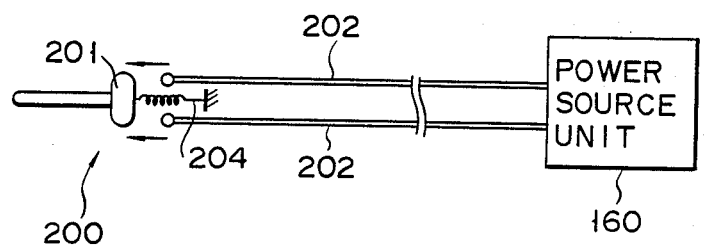
F I G. 27

4,867,141

MEDICAL TREATMENT APPARATUS UTILIZING ULTRASONIC WAVE

BACKGROUND OF THE INVENTION

A. Field of the Invention

The present invention relates to a medical treatment apparatus utilizing an ultrasonic wave and used for a treatment for breaking up, e.g., a stone formed in a living body.

B. Description of the Prior Art

Conventional ultrasonic treatment apparatuses are known to break up various stones (e.g., a gallstone formed in a bile duct and ureteral stones formed in a ureter, a renal pelvis, and calyxes) formed in living bodies.

Such a conventional ultrasonic treatment apparatus comprises a vibration generator and an insertion portion with a vibration transmission member. Various stones formed in living bodies are broken up by ultrasonic vibrations transmitted by the vibration transmission member. In particular, in an ultrasonic treatment apparatus having a flexible vibration transmission member, an insertion portion is inserted in an arcuated portion such as a bile duct through a treatment channel of an endoscope.

The vibration transmission member of the above-mentioned ultrasonic treatment apparatus is made of a stainless pipe, a metal wire or the like. The inner wall of the endoscope channel is made of a resin tube such as a GORE-TUBE (GORE-TEX INC.). The vibration transmission member is inserted in a body cavity through the channel of the endoscope. In this case, the edge of the vibration transmission member undesirably damages the inner wall of the channel.

In a conventional ultrasonic treatment apparatus wherein the ultrasonic transmission member of the insertion portion is entirely enclosed with a cover, the inner wall of the channel is not damaged when the transmission member is inserted in the channel of the endoscope. However, when a stone or thrombus is to be eliminated, the efficiency of the vibration transmission from the distal end of the ultrasonic treatment to an object to be broken up is degraded. As a result, the object cannot be satisfactorily broken up.

SUMMARY OF THE INVENTION

It is an object of the present invention to provide a medical treatment apparatus with an insertion portion capable of being inserted in a channel of an endoscope without damaging the inner wall surface thereof and effectively transmitting ultrasonic vibrations to an object to be broken up (e.g., a stone).

In order to achieve the above object of the present invention, there is provided a medical treatment apparatus comprising vibration generating means for generating ultrasonic vibrations, and a vibration transmission member, having a distal end portion and a proximal end portion mounted on the vibration generating means, for transmitting the ultrasonic vibration generated by the vibration generating means. The medical treatment apparatus further comprises a cover member which surrounds the vibration transmission member and exposing means for exposing the distal end portion of the vibration transmission member outside the cover member.

In the ultrasonic treatment apparatus according to the present invention, therefore, when an object such as a stone or thrombus is to be broken up, the distal end portion of the vibration transmission member can be exposed outside the cover member and the ultrasonic vibrations can be effectively transmitted to the object. When the vibration transmission member is to be inserted in the endoscope channel and the body cavity, the cover member on the distal end of the vibration transmission member prevents damage to the inner wall surfaces of the endoscope channel and the body cavity. Therefore, there is provided a medical treatment apparatus which can be operated safely and easily.

BRIEF DESCRIPTION OF THE DRAWINGS

FIG. 4 is a partially cutaway side view showing a first modification of the medical treatment apparatus of the first embodiment;

FIG. 5 is a partially cutaway side view showing a second modification of the medical treatment apparatus of the first embodiment;

FIG. 6 is a sectional view showing part of an insertion portion according to a third modification;

FIGS. 12 and 13 are respectively partial sectional views showing other modifications of the vibration transmission member of the second embodiment;

FIG. 14 is a partially cutaway side view showing a medical treatment apparatus according to a third embodiment of the present invention;

FIG. 15 is a longitudinal sectional view showing a distal end portion of an insertion portion of the medical treatment apparatus shown in FIG. 14;

FIG. 16 is a longitudinal sectional view showing a distal end portion of an insertion portion according to a modification of the third embodiment;

FIGS. 25 and 26 are sectional views showing parts of a sliding pipe and an outer cover according to a fourth modification of the fourth embodiment;

FIG. 27 is a schematic view showing a switch according to the fourth modification of the fourth embodiment;

Detailed Description of the Preferred Embodiments

Figure 1:
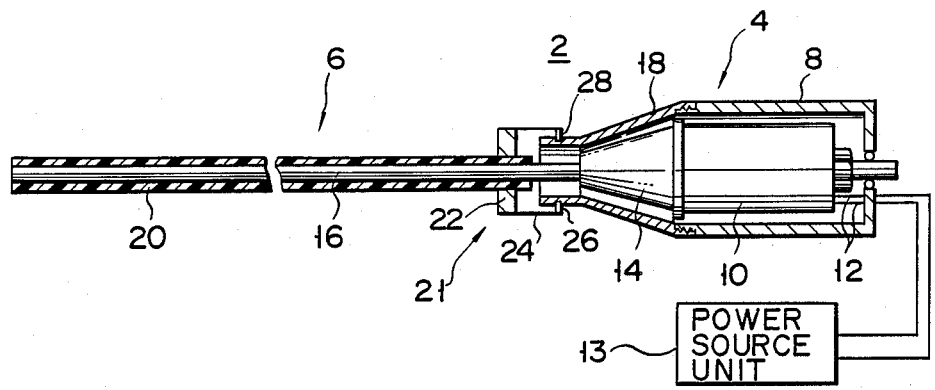
FIG. 1 is a partially cutaway side view showing a medical treatment apparatus according to an embodiment of the present invention.
Figure 2:
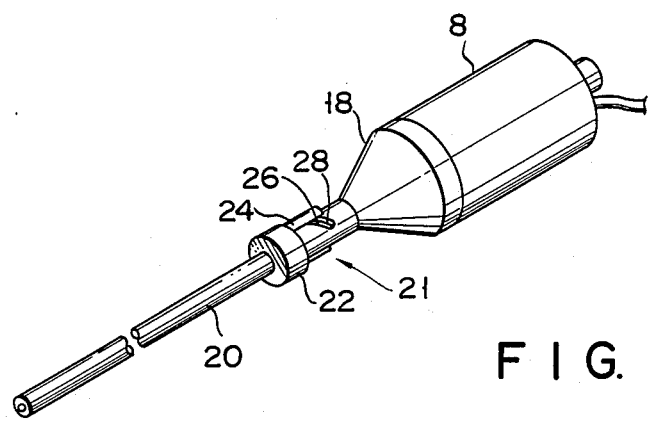
FIGS. 2 and 3 are perspective views of the medical treatment apparatus shown in FIG. 1.
Figure 3:
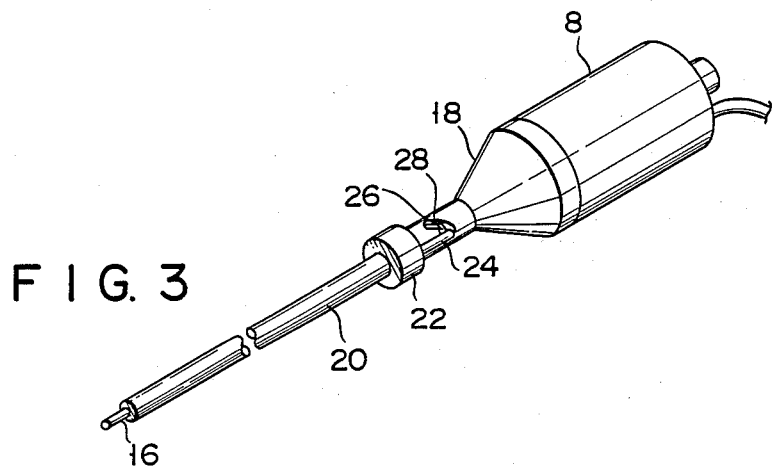

Preferred embodiments of the present invention will be described in detail with reference to the accompanying drawings. FIGS. 1 to 3 show a first embodiment of the present invention. Ultrasonic treatment apparatus 2 of this embodiment comprises holding portion 4 and insertion portion 6 to be inserted into a body cavity. Langevin ultrasonic vibrator 10 is arranged in rear case 8 in holding portion 4. Power cord 12 is connected to vibrator 10. Cord 12 extends through the rear end wall of rear case 8 and is connected to power unit 13. The proximal end of conical horn 14 is connected to the distal end of vibrator 10. Flexible vibration transmission member 16 made of a thin metal member is fixed to the distal end of horn 14. Front case 18 having a conical shape corresponding to the outer shape of horn 14 and a cylindrical distal end surrounds the outer surface of horn 14. The rear end of front case 18 is threadably engaged with the front end of case 8 through threads formed therein. Vibrator 10 and horn 14 are supported and fixed by cases 8 and 18 which surround these members as a whole. Tube-like cover 20 made of a tube of a resin such as vinyl chloride or a hydrofluoric resin covers the outer surface of vibration transmission member 16 connected to the distal end of horn 14. Mounting pipe 22, as exposing means 21, is fixed to the rear portion of cover 20. A pair of leaf springs 24 are mounted around pipe 22 at positions symmetrical about the pipe axis. Pins 26 extend inward from the rear ends of springs 24. A pair of cam grooves 28, as exposing means 21, are formed in the outer surface of the cylindrical portion at the distal end of case 18 which surrounds horn 14. Cam grooves 28 respectively engage with pins 26 of springs 24. As shown in FIGS. 2 and 3, cam grooves 28 are inclined at a predetermined angle with respect to the axis of the cylindrical portion. Therefore, when mounting pipe 22 is rotated from the state shown in FIG. 2 in a predetermined direction, pins 26 are rotated along cam grooves 28. Pipe 22 and cover 20 are then retracted, and thus the distal end of vibration transmission member 16 covered by cover 20 is exposed outside, as shown in FIG. 3. When pipe 22 is rotated in the opposite direction, transmission member 16 is retracted inside cover 20.

Figure 28:
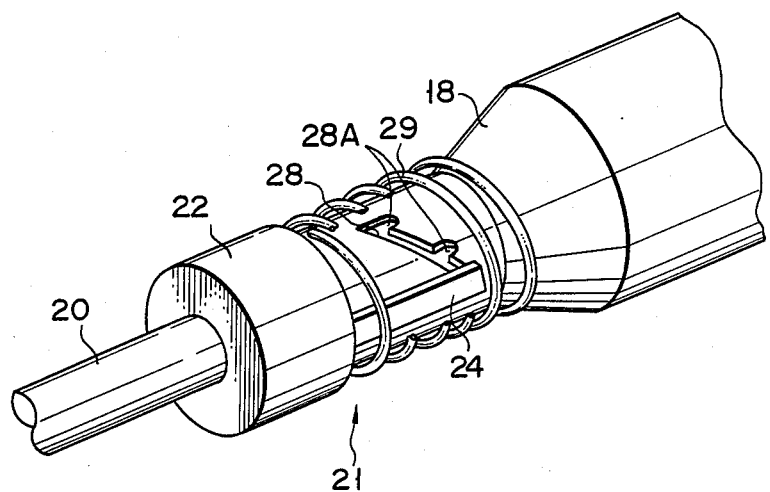
FIG. 28 is a perspective view showing another modification of the medical treatment apparatus shown in FIG. 1.

In the first embodiment, two leaf springs 24 each with pin 26 are mounted on mounting pipe 22 of cover 20. However, the number of springs is not limited to two, but can be increased to three or more. In this case, the number of cam grooves corresponds to the increased number of springs, and these cam grooves are formed in the cylindrical portion of case 18. As shown in FIG. 28, a plurality of clicks 28A can be formed at one side portion of each cam groove 28, and a coil spring 29 can be mounted between pipe 22 and case 18.

The operation of the ultrasonic treatment apparatus according to the first embodiment will be described below. If a gallstone is formed in a bile duct in a living body, for example, vibration transmission member 16 of ultrasonic treatment apparatus 2 is inserted in a flexible endoscope channel and a medical treatment is performed. In this case, since the channel is made from a resin such as a ductile expandable polytetrafluoroethylene (PIFE), the outer surface of vibration transmission member 16 is covered with cover 20 made of a resin such as vinyl chloride. Insertion portion 6 in ultrasonic treatment apparatus 2 is smoothly inserted in the channel, and the distal end of insertion portion 6 extends from the opening of the distal end of the channel. The distal end of the insertion portion comes near the stone formed in the living body. In order to expose the distal end of vibration transmission member 16 from cover 20, the operator turns pipe 22 mounted on cover 20. Pins 26 of leaf springs 24 are moved along cam grooves 28 formed in the cylindrical portion of the distal end of case 18, thereby exposing the distal end of transmission member 16 outside cover 20. Langevin vibrator 10 arranged in holding portion 4 is operated to generate ultrasonic waves.

Ultrasonic vibrations are amplified by horn 14, and the amplified vibrations are transmitted to the distal end through vibration transmission member 16 to break up the stone.

According to the first embodiment described above, cover 20, made of a resin such as vinyl chloride, is mounted on the outer surface of vibration transmission member 16 in insertion portion 6 of ultrasonic treatment apparatus 2. Therefore, the inner wall surface of the endoscope channel is not damaged by the metal edge of transmission member 16. Transmission member 16 can be smoothly inserted through the channel. When the stone is broken up by transmission member 16, the distal end of transmission member 16 is exposed from cover 20 and can be brought into direct contact with the stone, thereby achieving excellent vibration transmission efficiency. In the apparatus shown in FIG. 28, an exposing distance of transmission member 16 outside cover member 20 can be adjusted by clicks 28A.

FIG. 4 shows a first modification of the ultrasonic treatment apparatus of the first embodiment of the present invention. In this modification, an engaging method of pins 26 formed on leaf springs 24 in mounting pipes 22 mounted on cover 20 is different from that of the first embodiment. More specifically, pins 26 are engaged with annular grooves 30 formed on the outer surface of front case 18. In practice, a plurality of annular grooves 30 are formed at intervals along the axial direction of the cylindrical portion. When insertion portion 6 is to be inserted into the channel of the endoscope, pins 26 are engaged with the front annular groove 30 of the cylindrical portion. When the distal end of vibration transmission member 16 is to be exposed, pins 26 are engaged with rear annular groove 30. Other arrangements of the first modification of the first embodiment are the same as those of the first embodiment, and a detailed description thereof will be omitted.

In this modification, pins 26 can be slid between two annular groove of the cylindrical portion to cover vibration transmission member 16 with cover 20 or expose it therefrom.

FIG. 5 shows a second modification of an ultrasonic treatment apparatus of the first embodiment. In this modification, the outer surface of vibration transmission member 16 is covered with cover 20, and the distal end portion of transmission member 16 is further covered with material 32 (e.g., ceramic) as exposing means 21 to be broken by ultrasonic waves. The proximal end of cover 20 is directly fixed to the cylindrical portion of ultrafront case 18 in holding portion 4. Other arrangements of the second modification of the first embodiment are substantially the same as those of the first embodiment, and a detailed description thereof will be omitted.

The operation of the second modification of the first embodiment will be described below. When insertion portion 6 is inserted into the endoscope channel, the outer surface of vibration transmission member 16 is covered with cover 20. The distal end of transmission member 16 is covered with material 32 (e.g., ceramic) to be broken by ultrasonic waves. After insertion portion 6 is inserted into the channel and the distal end portion of insertion portion 6 appears from the opening of the channel, ultrasonic vibrations are transmitted to vibration transmission member 16. In this state, ceramic 32 mounted on the distal end of cover 20 is broken to expose the distal end of transmission member 16. Therefore, the distal end of transmission member 16 can be directly brought into contact with the stone in the living body. In this case, broken ceramic 32 and the broken up stone are removed by a suction unit (not shown) outside the body.

According to the second modification, the distal end of the vibration transmission member is not exposed by reciprocating the cover, unlike in the first embodiment and the first modification thereof. The distal end of the vibration transmission member is exposed by transmitting ultrasonic waves thereto. For this reason, operability of the ultrasonic treatment apparatus ca be improved.

FIG. 6 shows a third modification of the first embodiment. The structure of this modification is substantially the same as that of the second modification, and only different arrangements will be described. The outer surface of vibration transmission member 16 constituting insertion portion 6 in ultrasonic treatment apparatus 2 is covered with cover 20. The distal end portion of transmission member 16 is covered with film 34 of a resin such as vinyl chloride.

The operation of the third modification of the first embodiment will be described below. In order to heat a portion near the distal end of vibration transmission member 16 in insertion portion 6 inserted into the endoscope channel, the ultrasonic vibration frequency is controlled. The film is melted by heat caused by ultrasonic vibration, and the exposed distal end is brought into direct contact with the stone. The frequency of ultrasonic vibrations is switched to a suitable maximum frequency to break up the stone.

The same advantages as in the third modification can be obtained in the second modification.

In each of the first embodiment and the modifications thereof, a rod-like member such as a metal wire is used as the vibration transmission member. However, the vibration transmission member is not limited to the rod-like member but can be extended to a stainless pipe having a small diameter to obtain the same advantage as described above. When a stainless pipe is used, it has a through-hole at its center. This through hole can be used as a suction hole. Alternatively, the channel of the endoscope may be used as a suction hole. When the rod-like member is used, the channel is used as a suction hole. The cover need not be a tube-like cover but may be a mesh-like cover.

Figure 7:
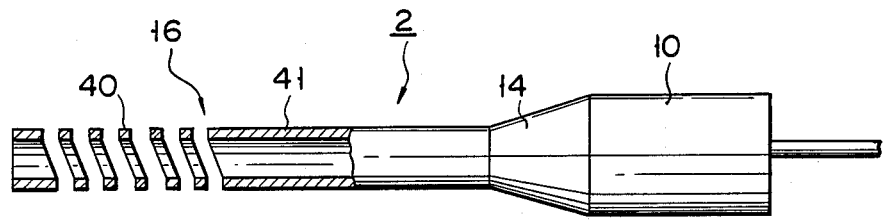
FIG. 7 is a partially cutaway side view showing a medical treatment apparatus according to a second embodiment of the present invention.

An ultrasonic treatment apparatus according to a second embodiment of the present invention will be described with reference to FIGS. 7 and 8. Ultrasonic treatment apparatus 2 shown in FIG. 7 comprises ultrasonic vibrator 10. Horn 14 and an ultrasonic transmission member, i.e., probe 16 are sequentially connected to vibrator 10. Probe 16 is made of a thin metal tube made of a metal with high rigidity such as stainless steel. Distal end section 40 of probe 16 comprises a coil which can be bent. A boundary between proximal end section 41 and distal end section 40 of probe 16 is determined as a node position upon operation of probe 16. The distal end face of probe 16 is located as a loop position of the vibration. A case for surrounding ultrasonic vibrator 10 and horn 14 and a cover for surrounding probe 16 are not illustrated in FIGS. 7 and 10.

Figure 8:
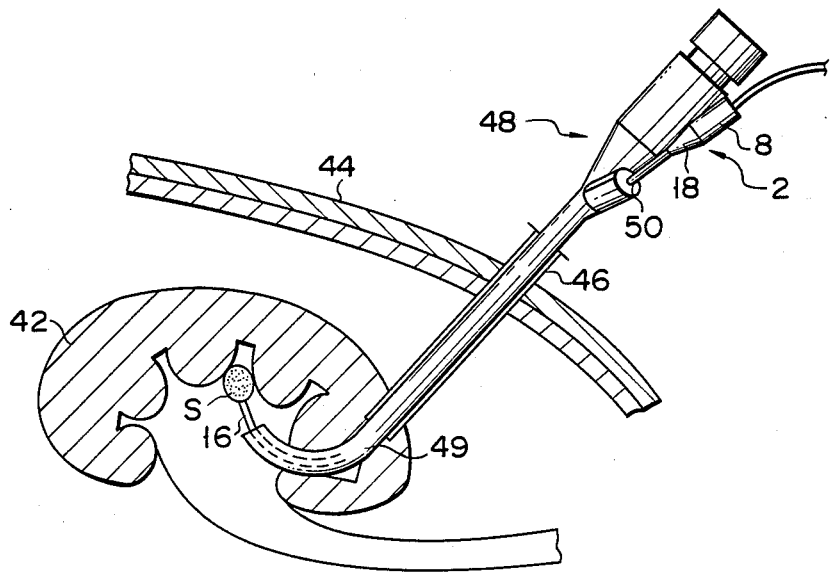
FIG. 8 is a partially cutaway side view showing an application state of the medical treatment apparatus shown in FIG. 7.

As shown in FIG. 8, a medical treatment wherein stone S formed in kidney 42 is broken with ultrasonic treatment apparatus 2 having the above arrangement will be described. Guide pipe 46 is inserted through body wall 44, and flexible insertion portion 49 of endoscope 48 is inserted in the body cavity through guide pipe 46. Probe 16 in ultrasonic treatment apparatus 2 is inserted from forceps port 50 of endoscope 48. After the distal end of probe 16 is slightly extended from the distal end face of insertion portion 49, the distal end portion of insertion portion 49 is slightly curved to bring the distal end of probe 16 into contact with stone S. In this state, ultrasonic vibrator 10 is energized to break up stone S with ultrasonic vibrations.

Coil section 40 of probe 16 may be thinner than the remaining section of probe 16.

Figure 9:
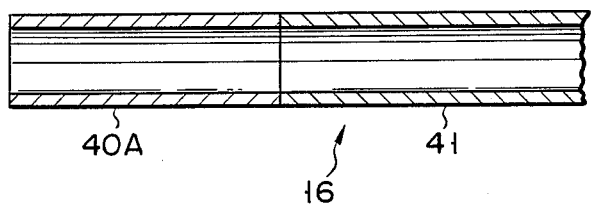
FIG. 9 is a longitudinal sectional view showing a vibration transmission member according to a first modification of the second embodiment.

FIG. 9 shows a modification of the vibration transmission member of the second embodiment. In this modification, proximal end section 41 of probe 16 is made of a stainless alloy having high rigidity (longitudinal modulus of elasticity $E \approx 20,000$ kg/mm$^2$). Distal end section 40A is made of a titanium alloy having low rigidity (longitudinal modulus of elasticity $E \approx 10,000$ kg/mm$^2$). The titanium alloy portion has flexibility. In this modification, the boundary between the proximal and distal end sections is located at the node position, and the distal end face is located at the vibration loop position in the same manner as in the second embodiment.

An Al-V titanium alloy (6Al-4V or 3Al-2.5V) is used for proximal end section 41 of probe 16, and an Ni-Ti alloy may be used for distal end section 40A.

Distal end section 40A of probe 16 may be made of a flexible synthetic resin.

Figure 10:
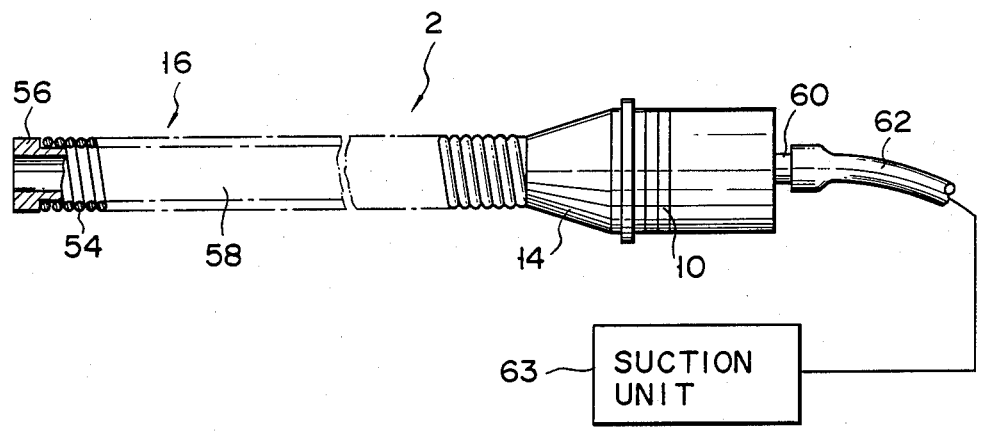
FIG. 10 is a partially cutaway side view showing a second modification of the medical treatment apparatus of the second embodiment.

FIG. 10 shows a second modification of the ultrasonic treatment apparatus of the second embodiment. In this modification, ultrasonic transmission member 16 comprises coil 54 obtained by winding a metal wire. Coil 54 has a circular or oval cross section. Cylindrical distal end tip 56 is fixed to the distal end of ultrasonic transmission member 16. Suction path 58 is formed inside ultrasonic transmission member 16. Suction path 58 is connected to suction mouthpiece 60 through a path (not shown) extending inside ultrasonic vibrator 10. Suction tube 62 is connected to suction unit 63.

When ultrasonic treatment apparatus 2 according to the second modification is used, ultrasonic transmission member 16 is introduced into the body cavity directly or through an endoscopic sheath or catheter. Ultrasonic vibrations are generated by ultrasonic vibrator 10 and amplified by horn 14. The amplified ultrasonic vibrations are transmitted to ultrasonic transmission member 16. Tip 56 formed at the distal end of ultrasonic transmission member 16 is brought into direct contact with a portion of interest such as a thrombus in a blood vessel. The thrombus is then eliminated. At the same time, suction unit 63 is operated to remove the thrombotic tissue through suction path 58, suction mouthpiece 60, and suction tube 62 in ultrasonic transmission member 16.

Since ultrasonic transmission member 16 is made of coil 54, it has excellent flexibility and at the same time a large inner diameter of suction path 58 can be assured.

Figure 11:
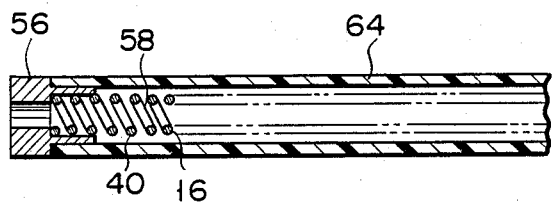
FIG. 11 is a longitudinal sectional view showing an insertion portion according to a third modification of the second embodiment.

FIG. 11 shows a third modification of the second embodiment. In this modification, flexible tube 64 is mounted on the outer surface of coil 54 of the second modification. Tube 64 improves air- and water-tight properties. Water-tightness can be assured even if the coil is not prepared by tightly winding the wire.

The ultrasonic transmission member may be made of a metal bellows or may be constituted by connecting a plurality of short pipes 66, as shown in FIGS. 12 and 13.

An ultrasonic treatment apparatus according to a third embodiment of the present invention will be described with reference to FIGS. 14 and 15. Ultrasonic treatment apparatus 2 shown in FIG. 14 comprises holding portion 4 and insertion portion 6. Langevin vibrator 10 as an ultrasonic vibrator is arranged inside outer case 8. Vibrator 10 comprises four piezoelectric elements 70, four electrode plates 72, front metal block 74, and rear metal block 76. Horn 14 is integrally mounted on metal block 74. Bolt 80 having axial liquid supply hole 78 is mounted at the axial centers of blocks 74 and 76. Bolt 80 is made of a titanium material having high tensile strength. Nut 82 is threadably engaged with the threaded rear portion of bolt 80. Cylindrical portion 84 is integrally formed with the rear end portion of bolt 80. Packing 88 is mounted in cylindrical portion 84 to seal the gap between rear wall 86 of outer case 8 and the rear end portion of bolt 80. The end part of cylindrical portion 84 extends through screw hole 90 formed in rear wall 86 and projects outside. Suction plug 94 is fitted with cylindrical portion 84 through O-ring 92. Front end portion 96 of suction plug 94 is threadably engaged with screw hole 90. Water supply tube 98 connected to water supply unit 97 is mounted on suction plug 94.

Temperature sensor 100 is arranged near Langevin vibrator 10, i.e., between the outer side of rear metal block 76 and holding portion 4. Both terminals 102 of temperature sensor 100 are connected to connector 104. One terminal 102 is detachably connected through connector 104 to wire 106 connected to electrode plate 72 of vibrator 10. The other terminal 102 is detachably connected through connector 104 to wire 108 of power cord 107 connected to power unit 105. Temperature sensor 100 detects the temperature of vibrator 10. When a measured temperature exceeds a predetermined temperature, a fuse is melted to interrupt the operation of vibrator 10.

As shown in FIG. 14, horn cover 18 which surrounds horn 14 is mounted at the distal end of outer case 8. Connecting cylinder 110 is mounted to the distal end of horn cover 18.

Figure 29:
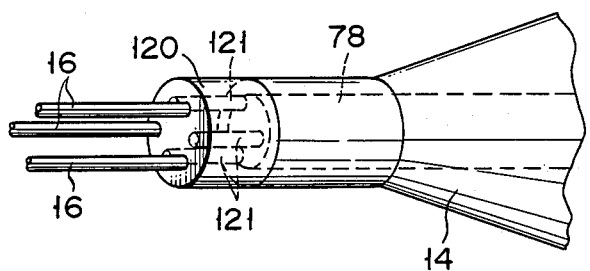
FIG. 29 is a perspective view showing another modification of a connecting portion shown in FIG. 14.

Insertion portion 6 of ultrasonic treatment apparatus 2 according to this embodiment comprises flexible tube 112 connected to the distal end of connecting cylinder 110. Supply path 116 communicating with liquid supply hole 78 and liquid supply mouthpiece 114 is formed inside tube 112. O-ring 118 is inserted between the distal end face of horn 14 and the inner surface of connecting cylinder 110. Supply path 116 is shielded from holding portion 4. A plurality of ultrasonic transmission members 16 are mounted on the distal end of horn 14 through connecting portion 120. Ultrasonic transmission member 16 is a wire having a small diameter and made of, e.g., a titanium alloy. Transmission member 16 may be solid or hollow. If a hollow member is used, the through hole formed therein communicates with liquid supply hole 78. Since each ultrasonic transmission member 16 has a small diameter, it has flexibility. As shown in FIG. 29, a plurality of through-holes 121 connecting supply path 116 with supply hole 78 can be formed in connecting portion 120. A perfusion liquid is supplied from liquid supply mouthpiece 114 disposed in connecting cylinder 110 to liquid supply path 116 by a space defined in tube 112.

Tube 112 is surrounded by outer tube 124. In other words, insertion portion 6 comprises a double tube structure. A space between tubes 112 and 124 defines suction path 126. Suction path 126 communicates with drain mouthpiece 128 disposed in connecting cylinder 110.

The distal end of each ultrasonic transmission member 16 slightly extends from the distal end face of tube 112. A liquid supply tube (not shown) is connected to liquid supply mouthpiece 114. A drain tube (not shown) is connected to drain mouthpiece 128.

The operation of the ultrasonic treatment apparatus according to the third embodiment will be described below. In order to break a stone, insertion portion 6 in ultrasonic treatment apparatus 2 is inserted in the body cavity through an endoscope channel or the like and a drive voltage is applied from power unit 105 to each piezoelectric element 70. As a result, ultrasonic vibrations are generated by Langevin vibrator 10. These vibrations are amplified by horn 14. The amplified vibrations are transmitted through each ultrasonic transmission member 16 of insertion portion 6 to stone 130 which is in contact with the distal end thereof. Therefore, stone 130 is broken by ultrasonic vibrations.

During the breaking of the stone, a perfusion liquid is supplied from water supply tube 98 to supply path 116 in tube 112 or hollow ultrasonic transmission members 16 through liquid supply hole 78. The perfusion liquid is supplied from the distal end of suction path 126 to the body cavity. The perfusion liquid in the body cavity is removed through suction path 126. At the same time, suction allows removal of broken pieces 132 of stone 130, as shown in FIG. 15. Pieces 132 are drained from drain mouthpiece 128 through the drain tube.

According to the third embodiment, the perfusion liquid flows toward the distal end in supply path 116 in tube 112 for accommodating ultrasonic transmission members 16 therein. Therefore, pieces 132 are not entered into supply path 116. Pieces 132 located in front of the opening of supply path 116 are pushed backward by the flow of the perfusion liquid and are moved to the inlet of suction path 126. Therefore, pieces 132 can be smoothly guided to suction path 126 and properly drained outside. Tube 112 accommodating ultrasonic transmission members 16 therein does not clog with pieces 132, thereby eliminating a disadvantage caused by clogging of the tube with pieces 132.

When the flow of the perfusion liquid is reversed, pieces 132 are drawn into tube 112 which receives ultrasonic transmission members 16 therein. Pieces 132 tend to be clogged in the tube to cause unnecessary bending of ultrasonic transmission members 16 and a load to act thereon. In this case, transmission energy is greatly attenuated and stone breakage performance is greatly degraded. However, since the perfusion liquid is flowed in the direction described above, the above drawback can be eliminated.

Since the perfusion liquid is supplied through tube 112, as shown in FIG. 15, the flow speed is maximum at the central portion of the flow. Ultrasonic transmission members 16 are concentrated at the center of tube 112 and tend not to be brought into contact with tube 112. Therefore, the distal end of each transmission member 16 can be accurately brought into direct contact with stone 130.

In the ultrasonic treatment apparatus according to the third embodiment, the opening of the distal end of outer tube 124 may be closed and suction port 134 may be formed on the wall surface of the distal end portion of outer tube 124, as shown in FIG. 16. If so, the diameter of the perfusion liquid flow can be increased.

Insertion portion 6 is not limited to the double tube structure, but can be extended to a multi-layered structure of three or more layers. In this case, the paths defined by the multi-layered structure may be used as supply, suction, and supply paths, respectively, from the inside. If the two inner paths are used as supply and suction paths, the outermost path may be used for a suction or supply path.

The suction path formed on the outermost portion of tube 112 is not limited to an annular path defined by tube 124 but may have any structure.

The insertion portion of the ultrasonic treatment apparatus according to the third embodiment may be applied to an apparatus for incising tissue of a living body.

Figure 17:
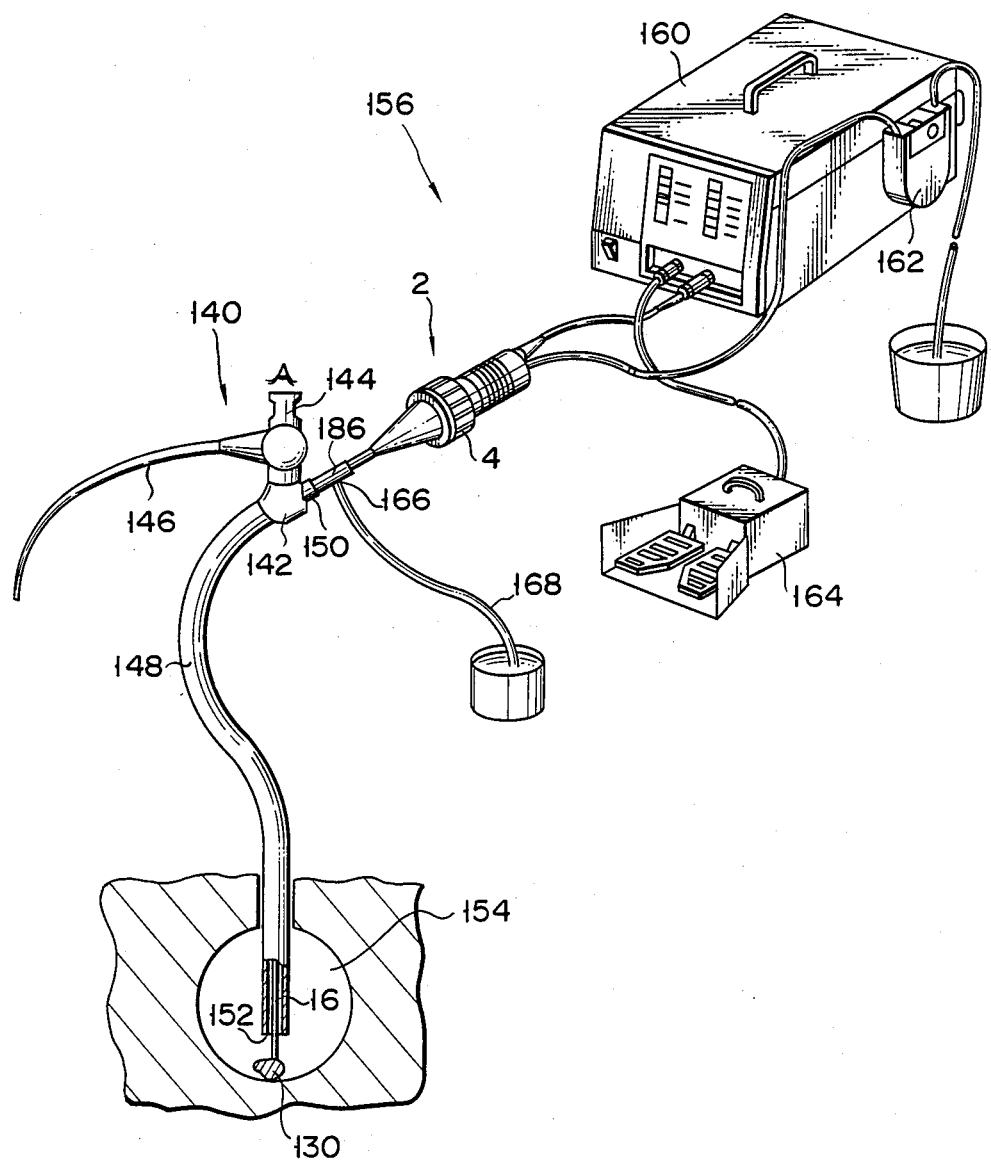
FIG. 17 is a perspective view of an ultrasonic treatment system with a medical treatment apparatus of a fourth embodiment of the present invention.

An ultrasonic treatment apparatus according to a fourth embodiment of the present invention will be described below. FIG. 17 shows an application state of the ultrasonic treatment apparatus according to this embodiment. Endoscope 140 shown in FIG. 17 comprises manipulation portion 142 and insertion portion 148. Manipulation portion 142 includes eyepiece 144, light guide universal cord 146, and channel port 150. A view in front of the distal end portion of insertion portion 148 can be observed from eyepiece 144 through a lens (not shown) and an image guide (not shown), both of which are arranged inside insertion portion 148.

Channel 152 communicating with channel port 150 extends from channel port 150 to the distal end of insertion portion 148.

In order to break stone 130, insertion portion 148 of endoscope 140 is inserted in body cavity 154, and ultrasonic transmission member 16 in ultrasonic treatment apparatus 2 in ultrasonic treatment system 156 is inserted from channel port 150. The distal end of transmission member 16 is brought into direct contact with stone 130 to apply ultrasonic vibrations to stone 130, thereby breaking stone 130. System 156 comprises holding portion 4 arranged at the rear end of ultrasonic transmission member 16 and connecting metal piece 186 for connecting holding portion 4 and manipulation portion 142 of endoscope 140. System 156 also comprises power unit 160 connected to the rear end of holding portion 4, perfusion pump 162, and foot switch 164 for operating power unit 160.

Ultrasonic transmission members 16 are inserted in channel 152 while they are covered with cover 20 made of a Teflon tube having high flexibility. The perfusion liquid supplied by perfusion pump 162 assures the field of view of endoscope 140 and cools ultrasonic transmission members 16. The perfusion liquid is delivered from pump 162 to body cavity 154 through holding portion 4 and is drained through channel 152, mouthpiece 166, and tube 168.

Figure 18:
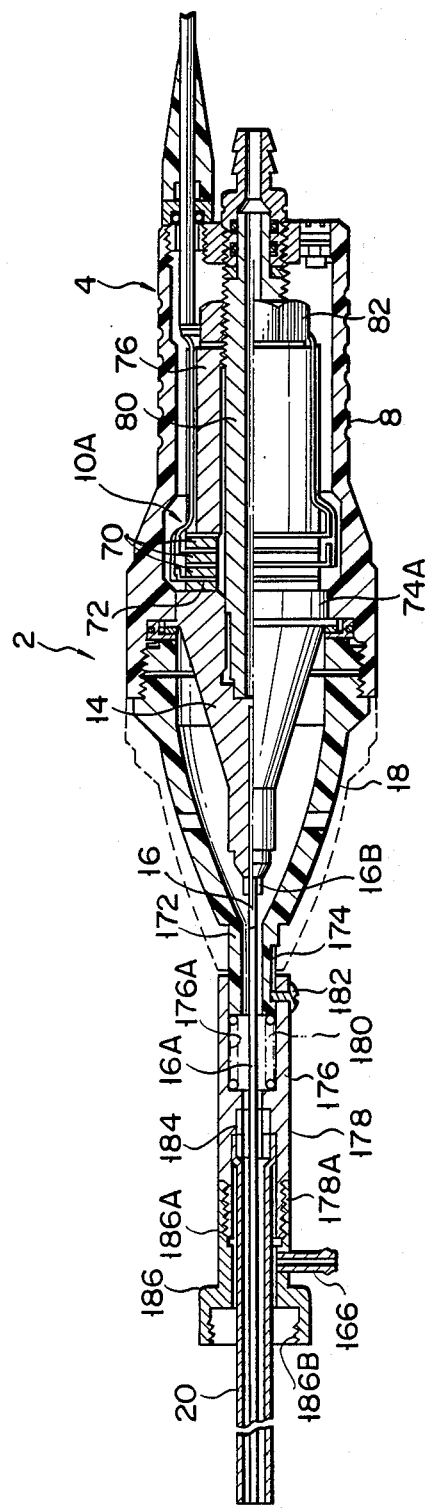
FIG. 18 is a partially cutaway side view showing the medical treatment apparatus according to the fourth embodiment of the present invention.
Figure 19:
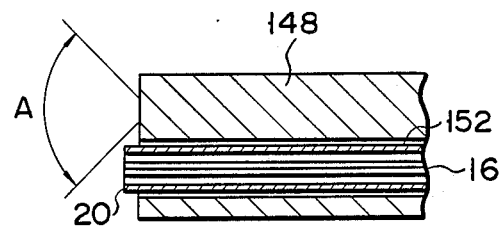
FIGS. 19 and 20 are respectively longitudinal sectional views showing a distal end portion of an endoscope insertion portion and a distal end portion of the medical treatment apparatus, both of which are illustrated in FIG. 17.
Figure 20:
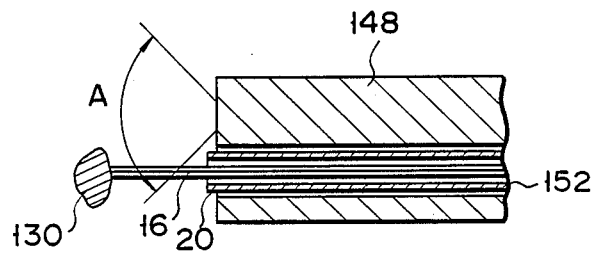

Ultrasonic treatment apparatus 2 according to the fourth embodiment of the present invention is illustrated in FIGS. 18 to 20.

Ultrasonic vibration section 10A and conical horn 14 having block section 74A corresponding to front metal block 74 in the above embodiment are accommodated in case 8 in holding portion 4 in ultrasonic treatment apparatus 2 shown in FIG. 18.

Figure 30:
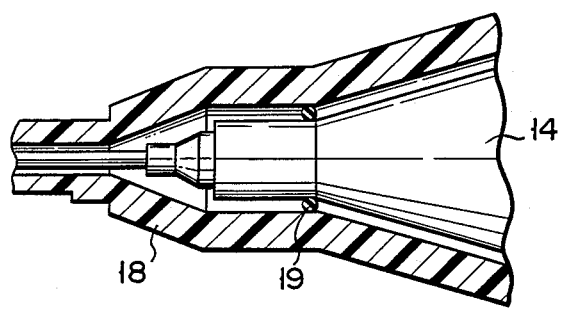
FIG. 30 is a partially cutaway side view showing another modification of the medical treatment apparatus shown in FIG. 18.

Front case 18 as a first cover is mounted at the front end of case 8 to surround the outer surface of horn 14. Case 18 is made of a material having relatively high rigidity (e.g., stainless). As shown in FIG. 30, O-ring 19 can be mounted between the inner surface of front case 18 and the outer surface of horn 14. Ultrasonic vibration section 10A comprises piezoelectric elements 70, electrode plates 72 alternately formed with elements 70 around bolt 80 mounted on the end face of metal block section 74A, and rear metal block 76 disposed behind elements 70 and plates 72. These members are tightened by nut 82 threadably engaged with the rear end portion of bolt 80.

Ultrasonic transmission member 16 is connected to the distal end of horn 14. Ultrasonic vibrations generated by ultrasonic vibration section 10A are transmitted to the distal end of transmission member 16. Transmission member 16 comprises two flexible long pipes 16A and two flexible short pipes 16B. Two long pipes 16A are used to increase mechanical strength of transmission member 16, and two short pipes 16B are used to effectively cool the perfusion liquid along long pipes 16A. The perfusion liquid is physiological saline or the like. The perfusion liquid supplied to the path inside vibration section 10A passes through transmission member 16 and cover 20 and is delivered to body cavity 154. The liquid is circulated to connecting metal piece 186 through a gap between cover 20 and channel 152. The liquid is then drained outside from mouthpiece 166 mounted on metal piece 186 to drain tube 168.

Slide pipe portion 172 is integrally formed with the distal end portion of front case 18. Slide groove 174 parallel to transmission member 16 is formed on the outer surface of portion 172. Outer cover 178 as the second cover is mounted in slide groove 174 formed on the outer surface wall of slide pipe portion 172 and is slidable therein along the longitudinal direction. Cover 178 comprises movable annular member 176. Engaging hole 176A is formed inside annular member 176. Coil spring 180 as a biasing member is housed inside annular member 176. Metal stopper 182 is threadably engaged with the edge of annular member 176. The distal end of metal stopper 182 is engaged with groove 174. Therefore, pipe portion 172 is normally biased backward by spring 180 with respect to outer cover 178. The movable range of pipe portion 172 is limited by stopper 182. Pipe 184 is fitted in the intermediate wall portion of outer cover 178. Cover 20 which covers ultrasonic transmission member 16 is connected to pipe 184.

Threaded portion 178A formed on the distal end portion of outer cover 178 is threadably engaged with threaded portion 186A of endoscope connecting metal piece 186. The inner diameter of annular metal piece 186 is larger than the outer diameter of cover 20. Liquid mouthpiece 166 is fixed to the intermediate portion of metal piece 186. Connecting threaded portion 186B is formed on the inner wall surface of the distal end portion of metal piece 186 to connect to endoscope channel port 150 shown in FIG. 17.

In the state shown in FIG. 18, front case 18 is separated from outer cover 178 by coil spring 180. For this reason, the distal end of ultrasonic transmission member 16 at the distal end portion of insertion portion 148 of endoscope 140 is located inside cover 20. In this state, transmission member 16 can be safely inserted into channel 152 of insertion portion 148 and body cavity 154 without damaging them. Ultrasonic treatment apparatus 2 can be attached to or detached from endoscope 140 by connecting metal piece 186.

When front case 18 is pushed to a position (indicated by the broken line in FIG. 18) against the biasing force of coil spring 180, the distal end portion of ultrasonic transmission member 16 projects from the distal end face of cover 20, as shown in FIG. 20, and can be brought into direct contact with stone 130 or the like. Therefore, stone breakage and thrombus elimination can be performed. In a state wherein the distal end portion of transmission member 16 projects from the cover, the distal end portion of transmission member 16 appears within the field of view of the endoscope, as indicated by reference symbol A in FIGS. 19 and 20. The operator can manipulate the ultrasonic treatment apparatus while checking the contact state between the stone and the distal end of transmission member 16.

Figure 21:
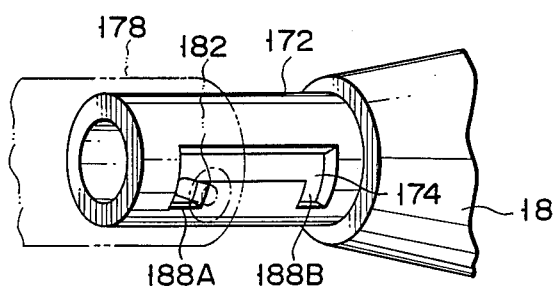
FIG. 21 is a perspective view showing a slidable pipe of a horn cap according to a first modification of the fourth embodiment.
Figure 31:
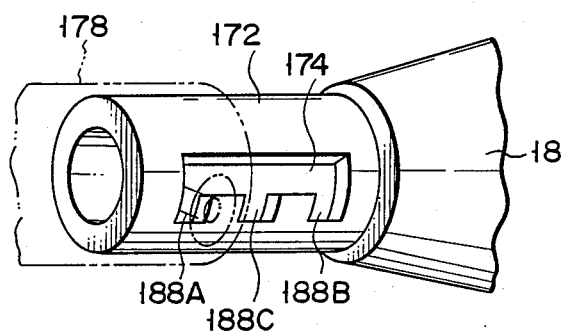
FIG. 31 is a perspective view showing another modification of a slide groove shown in FIG. 21.

FIG. 21 shows a first modification of the fourth embodiment. In this modification, engaging grooves 188A and 188B are respectively formed at the distal and proximal ends of slide groove 174 to lock ultrasonic transmission member 16 and cover 20 at a position where the distal end portion of ultrasonic transmission member 16 projects from the distal end face of cover 20 or at a position where transmission member 16 is housed inside cover 20. After front case 18 is moved forward, it is rotated to engage groove 188B with stopper 182 of outer cover 178. In this case, transmission member 16 is locked at a position where the distal end portion of transmission member 16 projects from the distal end face of cover 20. When stopper 182 is engaged with groove 188A, the distal end portion of transmission member 16 is held inside cover 20. As shown in FIG. 31, middle engaging groove 188C can be formed at the middle portion of slide groove 174 to lock transmission member 16 at the portion.

Figure 22:
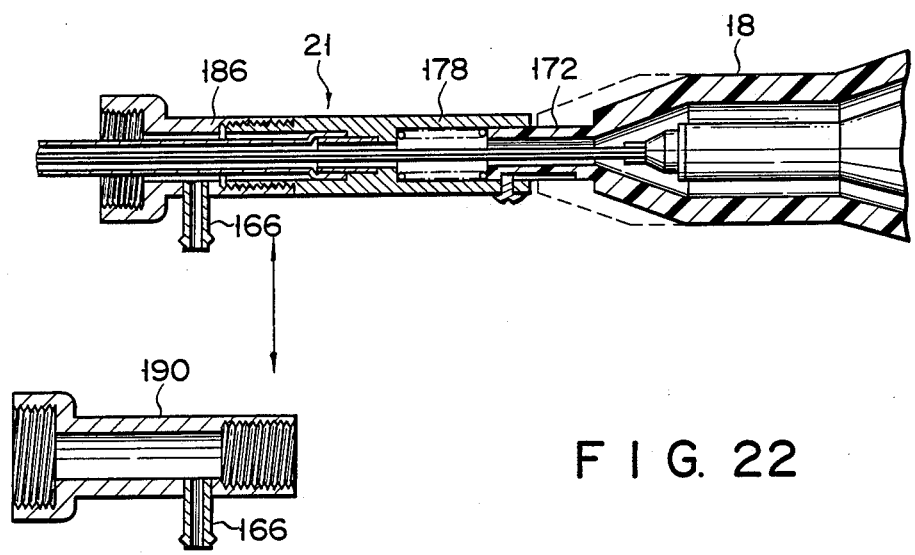
FIG. 22 is a longitudinal sectional view showing a metal piece for connecting an endoscope according to a second modification of the fourth embodiment.

As shown in FIG. 22, in the ultrasonic treatment apparatus according to a second modification of the fourth embodiment, another endoscope connecting metal piece 190 having a length different from that of metal piece 186 along the longitudinal direction may be used. Therefore, the ultrasonic treatment apparatus can be attached to various endoscopes with channels 152 of different lengths.

Figure 23:
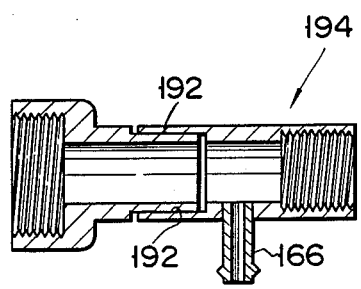
FIGS. 23 and 24 are longitudinal sectional views of metal pieces for connecting an endoscope according to a third modification of the fourth embodiment.
Figure 24:
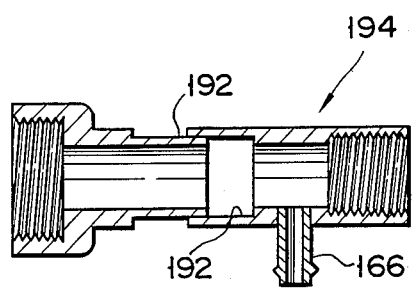

FIGS. 23 and 24 show a third modification, i.e., the structure of the endoscope connecting metal piece. Extendable connecting metal piece 194 according to this modification has click 192 so that the longitudinal length of metal piece 194 can be freely adjusted. Therefore, the ultrasonic treatment apparatus can be connected to endoscopes with channels 152 of different lengths without changing parts.

FIGS. 25 and 26 show a fourth modification of the fourth embodiment. In this modification, switch 200 shown in FIG. 27 is arranged in part of front end face 196 which abuts against rear end face 198 of outer cover 178 when front end face 196 of front case 18, i.e., ultrasonic transmission member 16 projects from cover 20. Switch 200 comprises switch member 201, a pair of lead wires 202 connected to power unit 160, and coil spring 204 for biasing switch 200 to the OFF position. Switch 201 is normally biased by coil spring 204 and is located at a position where switch member 201 projects from front end face 196 of front case 18. When front end face 196 comes close to rear end face 198, as shown in FIG. 26, the ends of lead wires 202 are electrically connected and power unit 160 is held in the ON state.

In the ultrasonic treatment apparatus having the switch described above, generation of ultrasonic vibrations can be prevented except for during treatments, thus assuring safety of the patients.

The present invention is not limited to the above-mentioned embodiments and modifications. Various changes and modifications may be made within the spirit and scope of the invention. The internal structure of holding portion 4 is not limited to the one described above. The present invention is applicable to all ultrasonic treatment apparatuses each having an ultrasonic vibrator and an ultrasonic transmission member for transmitting ultrasonic waves generated by the ultrasonic vibrator.

What is claimed is:

1. A medical treatment apparatus utilizing ultrasonic waves, comprising:
   vibration generating means for generating ultrasonic vibrations;
   a case retaining said vibration generating means, said case having a front end portion;
   vibration transmission means having a distal end portion and a proximal end portion which is mounted on said vibration generated means, for transmitting the ultrasonic vibrations generated by said vibration generating means;
   cover means surrounding said vibration transmission means and having a proximal end slidably mounted on the front end portion of said case; and
   bias means interposed between said case and cover means for biasing said cover means to extend away from said case so that the distal end portion of the vibration transmission means is within said cover means, and for yielding under force to permit sliding of the proximal end of the cover means on the front end portion of said case so that the distal end portion of the vibration transmission means protrudes from the cover means.

2. The apparatus according to claim 1, wherein said vibration generating means has a fluid-supplying passage, and said vibration transmission means has an elongated flexible pipe communicating with the fluid-supplying passage.

3. The apparatus according to claim 1, wherein said vibration generating means has a fluid-supplying passage, and said vibration transmission means has an elongated flexible probe and a short pipe communicating with the fluid-supplying passage.

4. The apparatus according to claim 1, wherein said cover means has a first cover member and a second cover member, the first cover member being coupled to the second cover member, the second cover member having one end portion to be connected to the inlet port of the channel of an endoscope, and the other end portion slidably mounted on the front end portion of said case.

5. The apparatus according to claim 1, wherein the cover means is made of resin.

6. The apparatus according to claim 2, further comprising:
   means for discharging a perfusion liquid from the distal end portion of said vibration transmission means through said fluid supplying passage and said pipe.

7. The apparatus according to claim 3, further comprising:
   means for discharging a perfusion liquid from the distal end portion of said vibration transmission means through said fluid supplying passage and said short pipe.

8. The apparatus according to claim 4, further comprising suction means attached to said second cover member, for suctioning the perfusion liquid.

* * * * *